United States Patent [19]

Pitt et al.

[11] 4,201,471

[45] May 6, 1980

[54] OIL CONCENTRATION DETECTOR

[75] Inventors: Gillies D. Pitt; Stephen I. N. Gregorig, both of Harlow, England

[73] Assignee: ITT Industries, Incorporation, New York, N.Y.

[21] Appl. No.: 933,051

[22] Filed: Aug. 11, 1978

[30] Foreign Application Priority Data

Aug. 26, 1977 [GB] United Kingdom .............. 36060/77

[51] Int. Cl.$^2$ ..................... G01N 33/28; G01N 21/00; G01N 21/26
[52] U.S. Cl. .................................... 356/70; 250/574; 250/575; 356/338; 356/73
[58] Field of Search ....................... 250/574, 575, 209; 356/70, 435, 442, 343, 73, 338

[56] References Cited

U.S. PATENT DOCUMENTS 3,810,695  5/1974  Shea ........................................ 356/73

Primary Examiner—Vincent P. McGraw
Assistant Examiner—Rodney Bovernick
Attorney, Agent, or Firm—A. Donald Stolzy

[57] ABSTRACT

A system for determining the concentration of oil in a mixture of oil and water including an aligned photocell and a displaced photocell spaced therefrom to receive direct and reflected and/or refracted light through a scatter cell from a laser. A logarithmic amplifier is connected from the aligned photocell because a logarithm of the output thereof is a linear function. The displaced photocell output is essentially linear over a typical range above 200 parts per million (ppm). The output of the logarithmic amplifier is essentially linear below about 200 ppm. The linear portion of each output is combined by a switch when the logarithmic amplifier output passes through a selected threshold level.

4 Claims, 5 Drawing Figures

OIL CONCENTRATION DETECTOR

BACKGROUND OF THE INVENTION

This invention relates to electro-optical systems, and more particularly to a detector for producing an output signal proportional to the concentration of oil in a mixture of oil and water.

PRIOR ART STATEMENT

The assignee of this application was assignee of a related copending application Ser. No. 844,220, filed Oct. 21, 1977, now U.S. Pat. No. 4,146,799 by G. D. Pitt and H. J. Smith for OIL CONCENTRATION DETECTOR. The said copending application discloses an oil-in-water detector arrangement including a scatter cell through which the water is allowed to flow, a semiconductor laser operable in the infrared region of the spectrum and coupled to one side of the cell, and one or more photocells arranged at an angle of zero or more degrees to the laser beam so as to detect direct and scattered laser light, the latter being reflected or refracted from oil droplets in the water.

Automatic gain control circuitry is described in the said copending application. This circuitry is employed to operate over the range of oil concentration, e.g. over 0–200 parts per million (ppm), for which the output of the light-scattering cell is directly proportional to the oil concentration. This arrangement, however, produces a non-linear output above the 0–200 ppm range, and all other prior art oil-in-water meters of the light-scattering type are limited to the detection of oil levels within this range.

SUMMARY OF THE INVENTION

According to the present invention, there is provided a system for detecting oil in water, said system comprising: a scatter cell to receive a fluid mixture; source means to direct a beam of light through said scatter cell; a first photocell in alignment with said beam on the side of said scatter cell opposite the side on which said source means is located; a second photocell spaced from said first photocell to receive scattered light in a direction different from that in which said first photocell receives light; direct means for producing a first electrical signal of a magnitude which is a logarithmic function of the output of said first photocell; scatter means for producing a second electrical output signal of a magnitude directly proportional to the output of said second photocell; and electrical switch means for producing an output proportional to the concentration of oil at a predetermined terminal by switching only said second electrical signal to said terminal until one of said first and second electrical signals passes through a predetermined threshold level, and then switching only said first electrical signal to said terminal so long as said one electrical signal does not pass through said level in the reverse direction.

BRIEF DESCRIPTION OF THE DRAWINGS

In the accompanying drawings which illustrate exemplary embodiments of the present invention.

DESCRIPTION OF THE PREFERRED EMBODIMENT

Figure 1:
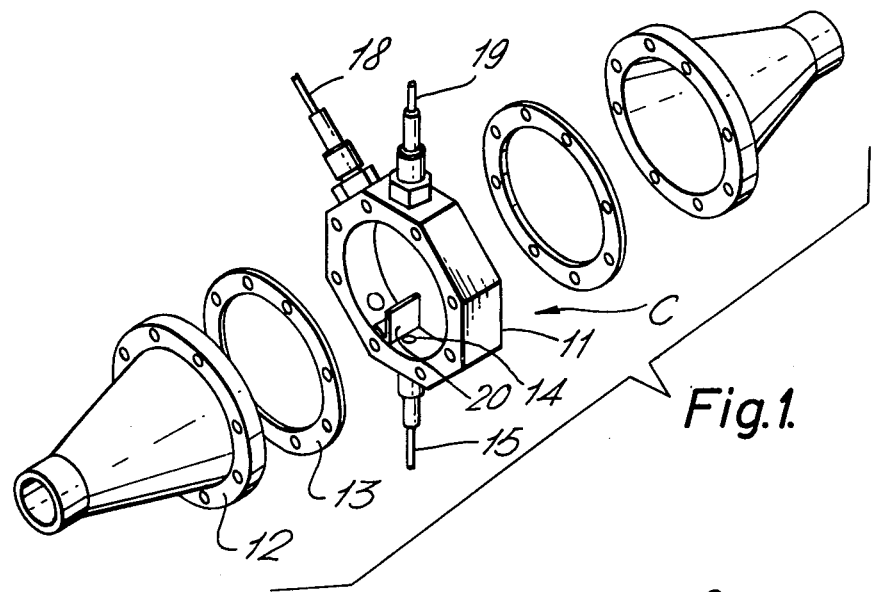
FIG. 1 is an exploded perspective view of a light-scattering cell constructed in accordance with the present invention.
Figure 2:
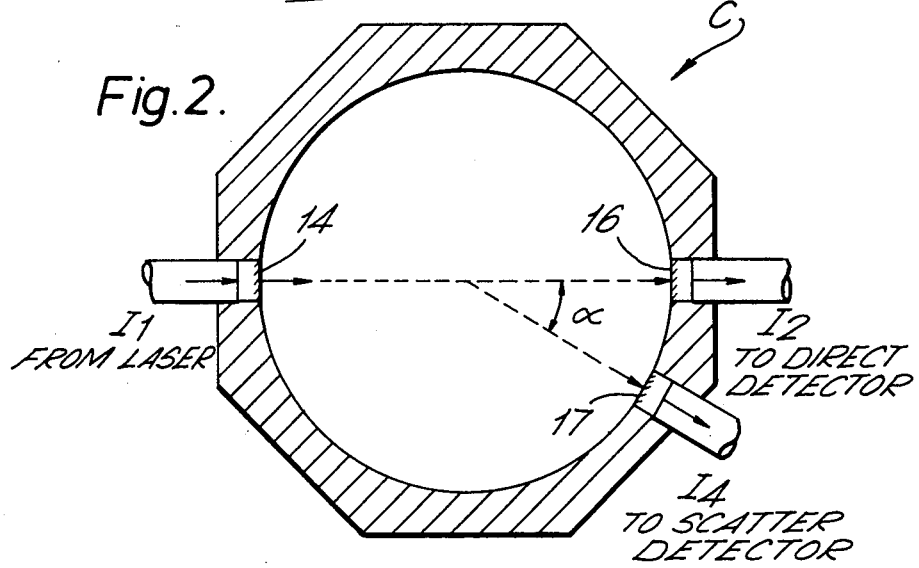
FIG. 2 is a transverse sectional view of the cell showing light paths through the cell.
Figure 3:
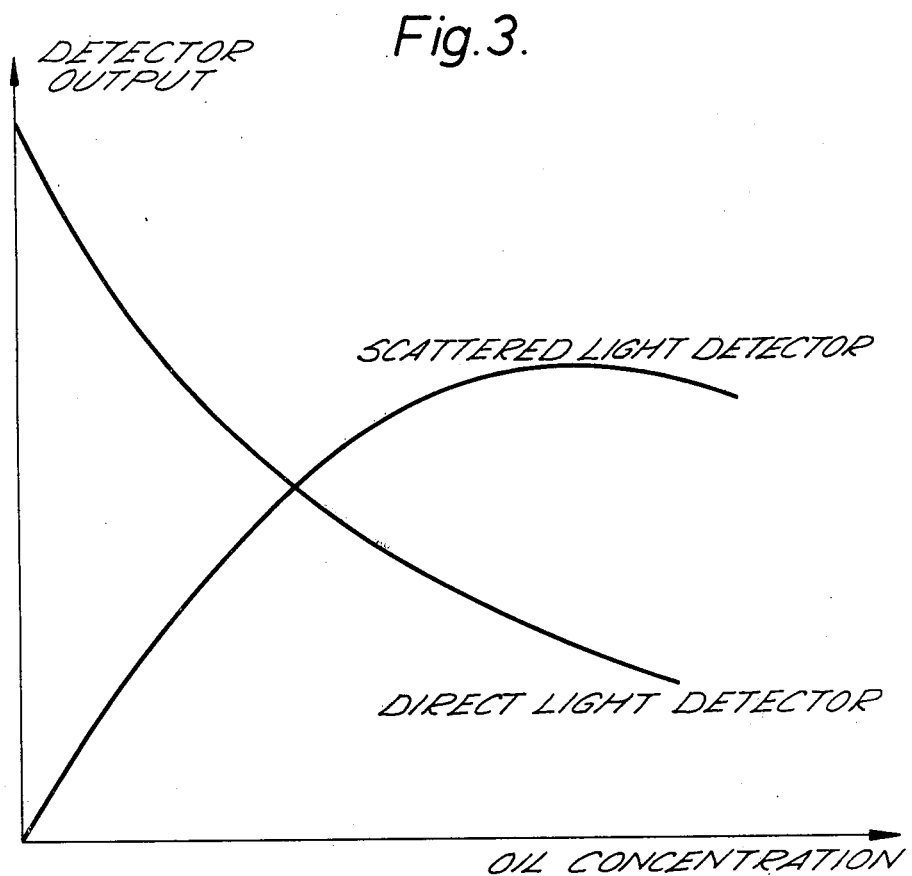
FIG. 3 is a graph of curves characteristic of the operation of the present invention.

Referring to FIGS. 1 to 3 the detector and measurement arrangement involves a light-scattering cell C including a central annular body 11 to which frustroconical conduits 12 are secured via gaskets 13. Light, e.g. from a gallium arsenide laser (not shown), is fed to light entry port 14 (FIG. 2) of the cell C via a first optical fiber 15 (FIG. 1) and is fed via light ports 16 and 17 to fibers 18 and 19 which in turn are coupled to photo-detectors, i.e. photocells. An inwardly directed plate member 20 prevents the light beam entering the cell C from directly illuminating the end of the fiber 18 so as to reduce spurious reflections.

As shown in FIG. 2, light from the entry port 14 is detected as a "straight through" signal via exit port 16 and at an angle $\alpha$ to the light path via exit port 17. The curves of FIG. 3 show typical responses to detectors coupled to ports 16 and 17, respectively. In the presence of oil droplets, the direct beam drops in intensity in a negative exponential or logarithmic manner. The scattered light increases substantially linearly at first, but at higher oil levels it reaches a maximum and then decreases. In the arrangement described herein, this maximum occurs at about 300–400 parts per million of oil.

It has been found that the scattered output responds less to the pressure of solid contaminants such as rust or sand than the "straight through" output. For example, if 1000 parts per million of rust having a particle size of 4 microns is passed through the system, the direct beam output typically registers the equivalent of 300 parts per million of oil, whereas the scattered output registers only 150 parts per million. Thus there is a considerable advantage in using the scattered output at low oil levels so as to minimize the effect of sand and rust.

It has been discovered, in accordance with the present invention, that the whole 1000 parts per million range can be covered by changing the detection mode from "straight through" to scatter. Thus the linear increase of the scatter output is used, but when the attenuation of oil droplets becomes greater than the scatter effect and the output approaches a maximum, an automatic change-over to "straight through" detection is effected. The attenuation of the direct beam is linearized using a logarithmic amplifier.

A further problem encountered with techniques relying on optical windows in contact with the oil water is that the windows themselves become dirty, causing the calibration of the system to change. Prior art methods continuously monitor the signal from the direct output and use this to dynamically compensate the signal from the scatter detector. At high oil levels, however, the extreme attenuation results in a highly non-linear output. The present arrangement minimizes this problem with an automatic gain control (AGC) circuit which is operational only when it is known that the system contains clean water.

It can be shown that the absorption A of the liquid in the cell is given by the equation:

$$A = \log I_o - \log I_t$$

where Io is the input light and It is the output light.

If Io is maintained constant and A is proportional to the oil concentration C, then $$C = K \log Io - K \log It$$

where K is a constant.

Thus to obtain an output oil concentration reading, the "straight through" signal of the cell C must be fed to an amplifier having a logarithmic response. Also as the windows become dirty, the system adjusts the signal amplifiers to that they operate on the same portion of the response curves.

Figure 4:
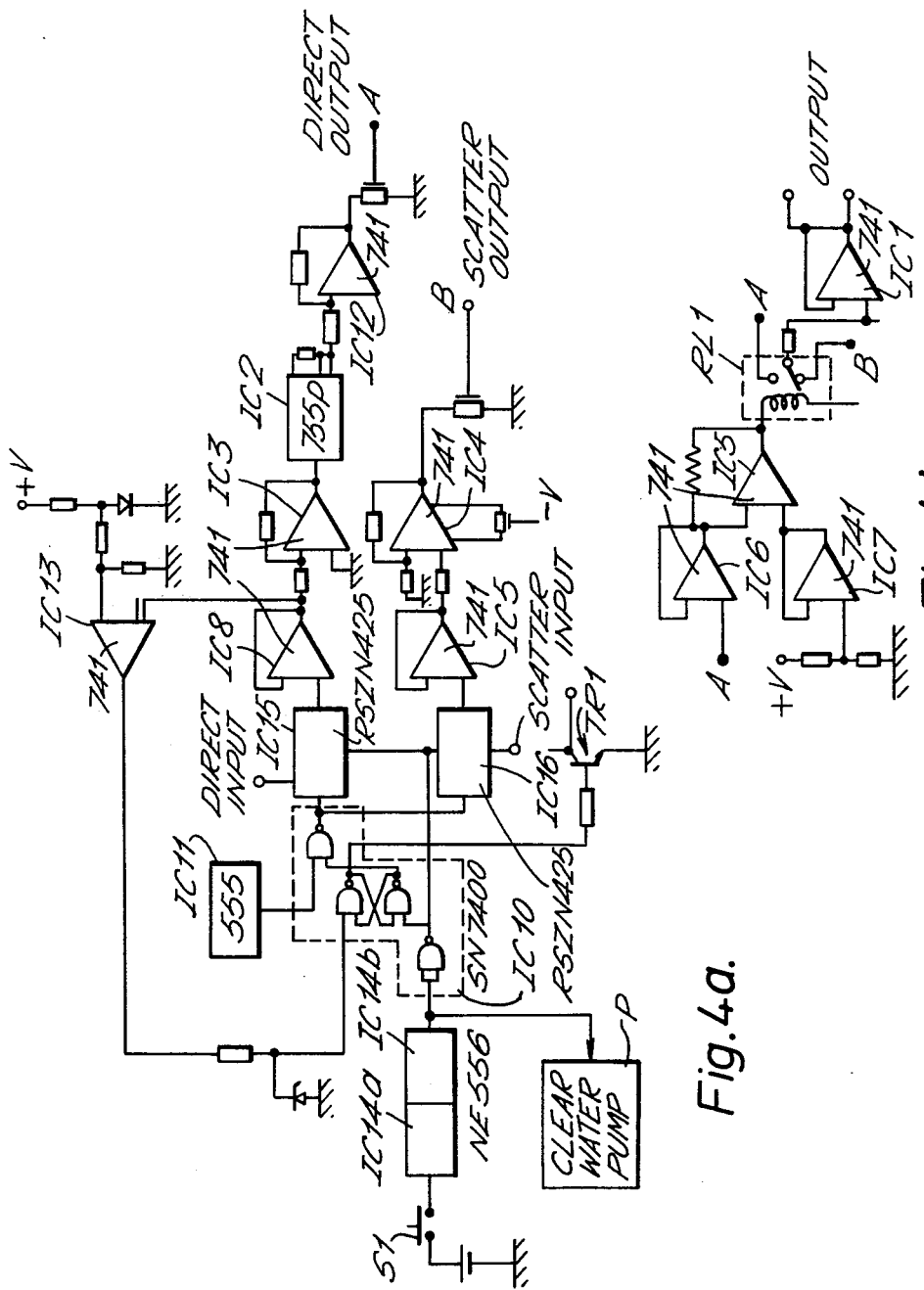
FIG. 4 is a schematic diagram of an amplifier and gain control circuitry of the present invention.
Figure 5:
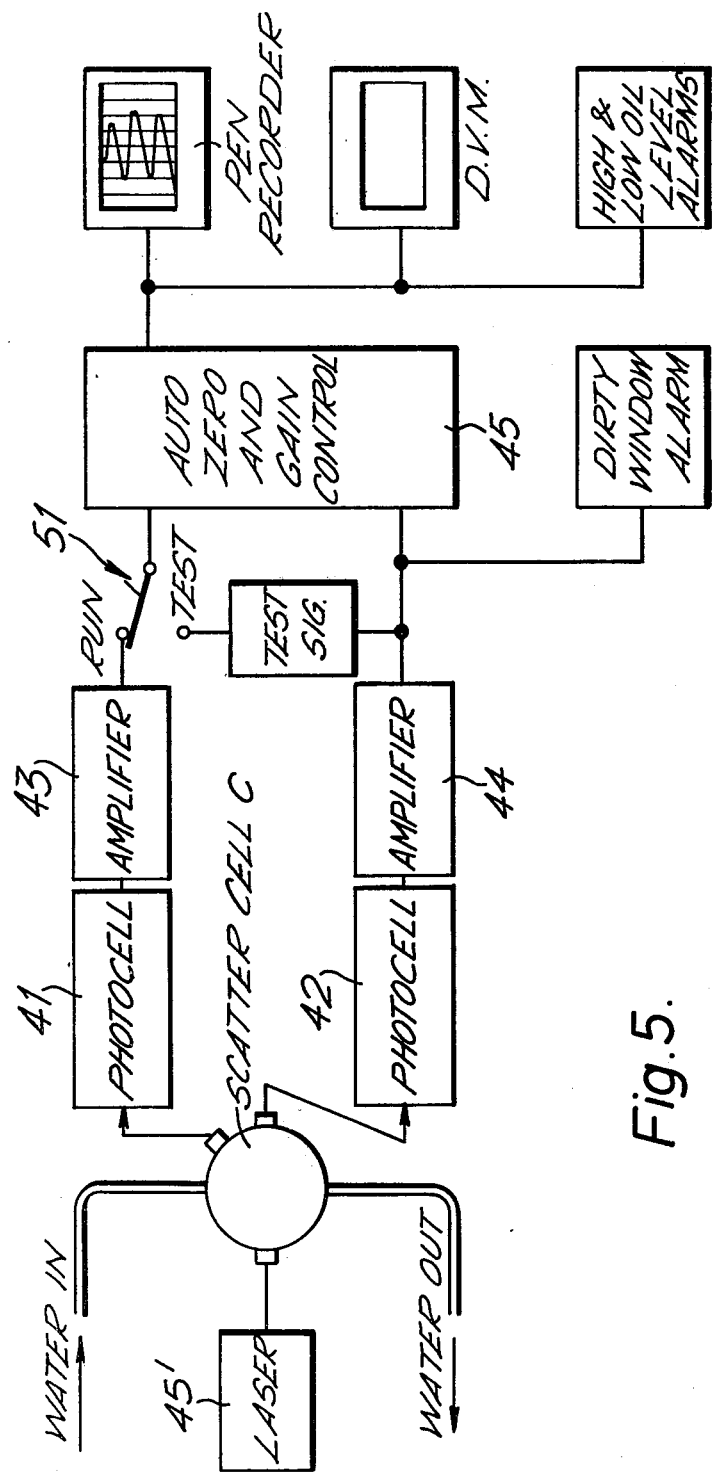
FIG. 5 is a block diagram of the circuit of FIG. 4.

The detector and output circuitry is shown in FIGS. 4 and 5 and comprise photodetectors 41 and 42, detector amplifiers 43 and 44, an automatic gain control system 45, and a solid state laser 45'. Control of the detector circuitry is effected by the automatic gain control system.

The AGC system has a dual digital-to-analog converter (DAC) shown as IC15 and IC16. A suitable device for this purpose is the integrated circuit type ZN425E (manufactured by Ferranti Ltd.) and includes an 8-bit counter for each input. The output of the converter is given by:

$$\frac{n \cdot V_{ref}}{256}$$

where $V_{ref}$ is the corresponding input voltage and n is the number of pulses (up to 256) input to the counter.

When calibration of the circuitry is required, a switch S1 (FIG. 4) is temporarily closed setting a timer IC14, which may be an NE555, one output of which enables a flushing valve (not shown) in a pump P which feeds clean water into the cell C. After clean water flushing has continued for a predetermined time, e.g. three minutes, the timer IC14 times out cutting off the clean water flow and generating an output pulse to reset the counters in IC15 and IC16 and to set a flip-flop in IC10, e.g. an SN7400. This allows pulses from IC11, which is an astable multivibrator, to clock the counters of IC15 and IC16. The output of IC15 is allowed to rise until it reaches 0.2 volts at which point IC13 which is wired as a comparator changes state and triggers the flip-flop IC10 stopping any further pulses from reaching IC15 and IC16. By this means a logarithmic amplifier IC2, a 755P, is presented with a constant 'zero oil' voltage. The gain of the scattered light channel, i.e. IC4, is adjusted together with the "straight through" channel. In the event that one or more or all of the cell ports 14, 16 and 17 have become so dirty that the "straight through" input is less than 0.2 volts, IC13 does not change state and the flip-flop of IC10 is not triggered, thus switching on a warning light via output transistor TR1.

The circuitry including IC5, IC6 and IC7 is the range switching arrangement. Range switching takes place at an oil level of about 200 parts per million via a relay RL1.

It is not possible to check the calibration of the scattered light amplifier IC4, e.g. by introducing into the light path a filter corresponding to a predetermined concentration of oil. This is because, unlike the "straight through" signal path, if no oil is present, the output from the scattering detector is zero. Therefore, in order to check the correct calibration of the system, when calibration switch 51 (FIG. 5) is operated, a portion of the "straight through" signal is applied to the input of the scattering system. If the calibration remains correct, the resulting output signal should be constant.

The outputs A and B of the "straight through" and scatter amplifiers, respectively, are coupled to the change-over contacts of the relay, the output of which is connected to a buffer output amplifier IC1 (FIG. 4) feeding a chart recorder or a display.

In some applications, a further light exit port (not shown) may be provided in the cell so as to receive light scattered at a larger angle than that shown in FIG. 2. The output of a further detector coupled to this further exit port is compared with that of the detector receiving light scattered at the angle of α. In this way the effect of solid contaminant particles may be very much reduced.

The preferred light source for the detector arrangement is a gallium arsenide laser, the output wavelength of which is in the region of the infra-red spectrum beyond the water absorption band region. Such a laser used with high speed silicon photodetectors provides a very stable system with a low noise level. The laser can be controlled by a separate system where light is separately obtained via an optical fiber from the front or rear of the laser and is measured to provide a signal for increasing or decreasing the laser input as the device ages with time and temperature. Alternatively, a silicon detector strip can be placed in the laser encapsulation to provide the control signal.

What is claimed is:

1. A system for detecting oil in water, said system comprising: a scatter cell to receive a fluid mixture; source means to direct a beam of light through said scatter cell; a first photocell in alignment with said beam on the side of said scatter cell opposite the side on which said source means is located; a second photocell spaced from said first photocell to receive scattered light in a direction different from that in which said first photocell receives light; first means for producing a first electrical signal of a magnitude which is a logarithmic function of the output of said first photocell; second means for producing a second electrical output signal of a magnitude directly proportional to the output of said second photocell; and electrical switch means for producing an output proportional to the concentration of oil at a predetermined terminal by switching only said second electrical signal to said terminal until one of said first and second electrical signals passes through a predetermined threshold level, and then switching only said first electrical signal to said terminal so long as said one electrical signal does not pass through said level in the reverse direction.

2. The invention as defined in claim 1, wherein means are provided to indicate the magnitude of the signal appearing at said terminal.

3. The invention as defined in claim 1, wherein said one electrical signal is said first electrical signal.

4. The invention as defined in claim 3, wherein means are provided to indicate the magnitude of the signal appearing at said terminal.

* * * * *